United States Patent
Melsheimer et al.

(10) Patent No.: US 9,107,668 B2
(45) Date of Patent: Aug. 18, 2015

(54) EMBOLIC PARTICLE MIXING SYRINGE

(75) Inventors: Jeffry S. Melsheimer, Springville, IN (US); Kurt J. Tekulve, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 886 days.

(21) Appl. No.: 12/408,109

(22) Filed: Mar. 20, 2009

(65) Prior Publication Data

US 2009/0247985 A1    Oct. 1, 2009

Related U.S. Application Data

(60) Provisional application No. 61/039,317, filed on Mar. 25, 2008.

(51) Int. Cl.
| | | |
|---|---|---|
| A61M 37/00 | (2006.01) | |
| A61B 17/12 | (2006.01) | |
| A61J 1/20 | (2006.01) | |
| A61B 17/00 | (2006.01) | |
| A61M 5/145 | (2006.01) | |
| A61M 5/20 | (2006.01) | |
| A61M 5/315 | (2006.01) | |

(52) U.S. Cl.
CPC ..... *A61B 17/12022* (2013.01); *A61B 17/12109* (2013.01); *A61B 17/12186* (2013.01); *A61J 1/2096* (2013.01); *A61B 2017/00495* (2013.01); *A61J 2001/2062* (2013.01); *A61M 5/1454* (2013.01); *A61M 5/2033* (2013.01); *A61M 5/31505* (2013.01); *A61M 2005/31598* (2013.01)

(58) Field of Classification Search
CPC ................. A61M 5/19; A61M 2005/14513; A61M 2005/31598; A61M 5/16881; A61K 2300/00
USPC ............. 604/82–92, 135, 226, 231, 506, 191, 604/246
See application file for complete search history.

(56) References Cited

U.S. PATENT DOCUMENTS

| | | | |
|---|---|---|---|
| 3,905,366 A * | 9/1975 | Callahan et al. .............. 604/209 |
| 4,335,717 A * | 6/1982 | Bujan et al. ...................... 604/83 |
| 4,689,042 A | 8/1987 | Sarnoff et al. |
| 4,738,660 A | 4/1988 | Lucas |
| 4,755,169 A | 7/1988 | Sarnoff et al. |
| 4,983,164 A | 1/1991 | Hook et al. |
| 5,032,117 A | 7/1991 | Motta |
| 5,041,094 A | 8/1991 | Perego et al. |
| 5,147,323 A * | 9/1992 | Haber et al. .................. 604/191 |
| 5,286,258 A | 2/1994 | Haber et al. |

(Continued)

FOREIGN PATENT DOCUMENTS

WO       WO 03/063928 A2    8/2003

*Primary Examiner* — Bhisma Mehta
*Assistant Examiner* — Brandy S Lee
(74) *Attorney, Agent, or Firm* — Brinks Gilson & Lione

(57) ABSTRACT

A syringe device for agitating and delivering a liquid medication to a patient is provided. The device includes an injecting member, a first syringe, a second syringe and an accumulator. The first syringe is configured to provide the liquid medication to the device. The second syringe is configured to receive the liquid medication from the first syringe. The accumulator is biased to an empty position and cooperates with the second syringe to agitate the liquid medication back and forth between the second syringe and the accumulator. The second syringe is configured to move the liquid medication to the injecting member for patient delivery.

21 Claims, 11 Drawing Sheets

(56) References Cited

U.S. PATENT DOCUMENTS

| | | | |
|---|---|---|---|
| 5,298,023 A | 3/1994 | Haber et al. | |
| 5,707,365 A | 1/1998 | Haber et al. | |
| 5,785,682 A * | 7/1998 | Grabenkort | 604/82 |
| 5,800,374 A * | 9/1998 | Beyersdorf | 604/4.01 |
| 6,062,722 A | 5/2000 | Lake | |
| 6,132,400 A | 10/2000 | Waldenburg | |
| 6,274,090 B1 * | 8/2001 | Coelho et al. | 435/297.1 |
| 6,544,233 B1 * | 4/2003 | Fukui et al. | 604/191 |
| 6,645,181 B1 | 11/2003 | Lavi et al. | |
| 6,692,468 B1 | 2/2004 | Waldenburg | |
| 6,699,222 B1 | 3/2004 | Jones et al. | |
| 6,723,068 B2 | 4/2004 | Lavi et al. | |
| 7,018,365 B2 | 3/2006 | Strauss et al. | |
| 7,101,351 B2 | 9/2006 | Crawford et al. | |
| 7,138,106 B2 | 11/2006 | Evans et al. | |
| 7,270,648 B2 | 9/2007 | Kazemzadeh | |
| 2001/0056259 A1 | 12/2001 | Skinkle et al. | |
| 2002/0077589 A1 | 6/2002 | Tessari | |
| 2003/0036725 A1 | 2/2003 | Lavi et al. | |
| 2003/0216685 A1 | 11/2003 | Porter | |
| 2004/0092883 A1 | 5/2004 | Casey, II et al. | |
| 2004/0182788 A1 * | 9/2004 | Dorian et al. | 210/649 |
| 2007/0068594 A1 | 3/2007 | Fischer et al. | |
| 2007/0088252 A1 * | 4/2007 | Pestotnik et al. | 604/82 |
| 2007/0255204 A1 | 11/2007 | McLean et al. | |
| 2007/0265574 A1 | 11/2007 | Tennican et al. | |
| 2008/0110831 A1 * | 5/2008 | Tsai et al. | 210/645 |

* cited by examiner

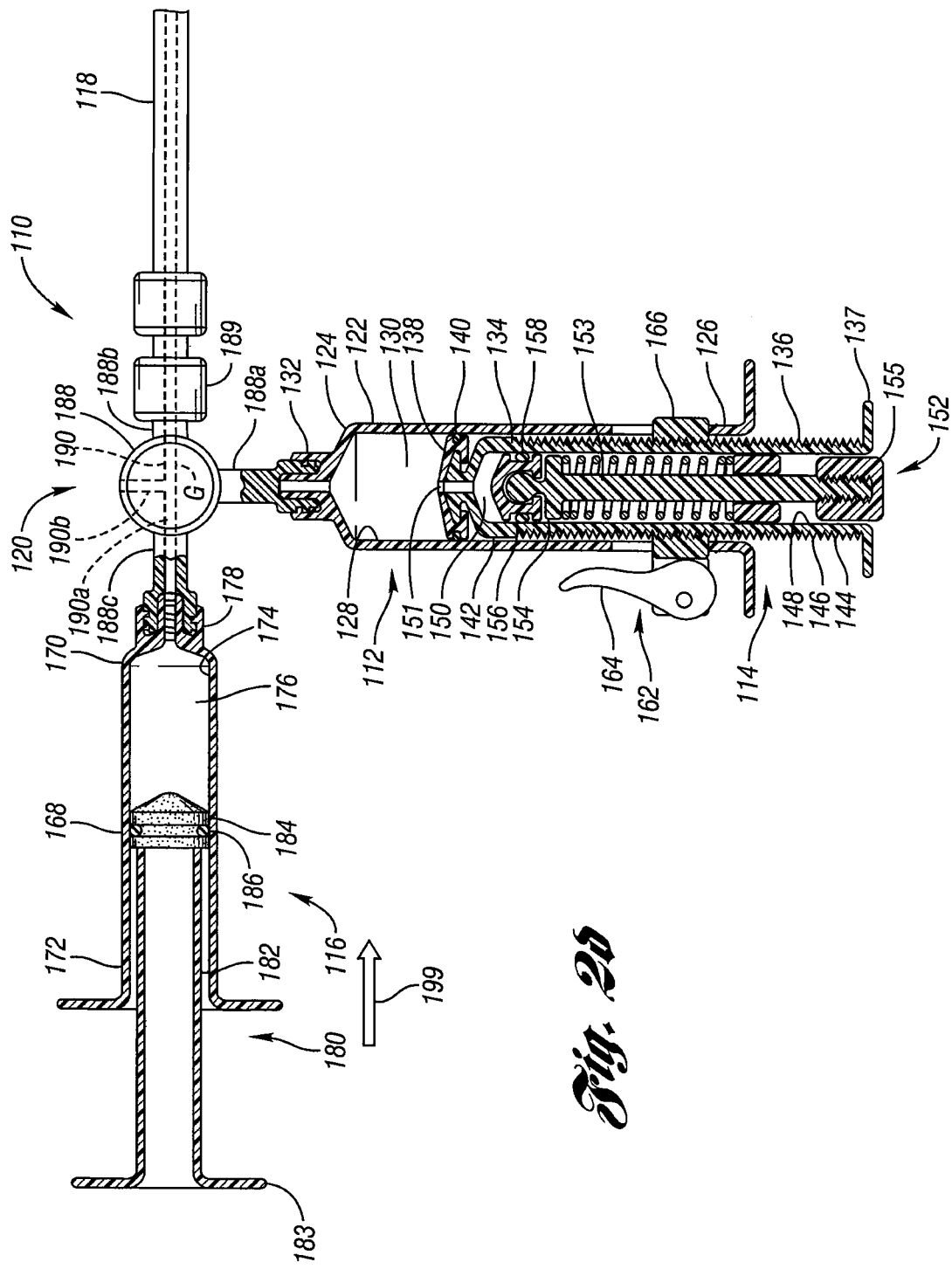

EMBOLIC PARTICLE MIXING SYRINGE

CROSS-REFERENCE TO RELATED APPLICATIONS

This application claims the benefit of U.S. Provisional Application Ser. No. 61/039,317 filed on Mar. 25, 2008, entitled "EMBOLIC PARTICLE MIXING SYRINGE," the entire contents of which are incorporated herein by reference.

BACKGROUND OF THE INVENTION

1. Field of the Invention

The present invention is related to medical devices. More particularly, the present invention is related to a syringe device for mixing and delivering liquid medications.

2. Background

It is desirable in many clinical situations to selectively occlude or embolize blood vessels for a variety of purposes, such as, the control or prevention of bleeding (e.g., organ bleeding, gastrointestinal bleeding, vascular bleeding, bleeding associated with an aneurysm). Embolization of blood vessels has been performed by employing certain polymer suspensions and particulates including silicone, metallic coils, sclerosing materials and the like to selectively block blood flow in the blood vessels.

One minimally invasive procedure for treating aneurysms, for example, involves the endovascular injection, via a syringe or catheter device, of a liquid embolic composition which accumulates in the aneurysm to occlude the aneurysm. The liquid embolic composition preferably comprises an aqueous vehicle, a biocompatible polymer and a water soluble contrast agent. The aqueous vehicle is miscible or soluble in blood or other body fluid and also carries the biocompatible polymer for the short period of time between their being brought together in a syringe, and the moment of delivery. The biocompatible polymer is selected to be suspensible in the aqueous vehicle by virtue of constantly being agitated, up until the time of injection. The water soluble contrast agent is mixed with the composition and permits the physician to fluoroscopically visualize catheter delivery of this composition.

Once the liquid embolic composition is injected into the aneurysm, the biocompatible polymer aggregates due to lack of turbulence and forms an embolic occlusion within the blood vessel, occluding the blood flow through the aneurysm.

A problem may arise, however, if the embolic composition accumulates within the syringe or catheter before delivery. Specifically, it has been found that the catheter line can become plugged due to premature aggregation of the biocompatible polymer. This plugging, of course, interferes with delivery of the composition to the specific site in vivo.

To prevent premature aggregation of the embolic particles within the composition and maintain uniform suspension, the composition should be mixed and agitated, before delivery. In general, a syringe device for agitating and delivering a liquid embolic composition to a vascular site comprises a larger syringe and a smaller high pressure syringe coupled together at their dispensing ends. The larger syringe provides the composition to the smaller syringe and the composition is passed back and forth to agitate the composition and maintain a uniform suspension of the embolic particles within the composition. The composition is passed back and forth by advancing and retracting the corresponding plungers. A disadvantage to using this type of syringe device is that its operation requires the operator to use two hands to manipulate the corresponding plungers of the two syringes, i.e., one hand for each plunger/syringe.

Thus, there is a need to provide an improved syringe device particularly useful for avoiding premature precipitation of a liquid embolic composition.

BRIEF SUMMARY OF THE INVENTION

Embodiments of the present invention provide a syringe device for mixing and delivering a liquid medication to a patient, and a method of mixing and delivering a liquid medication to a patient. Examples of the present invention allow for a more efficient and easier way of both mixing and delivering liquid medications, such as liquid embolic compositions, using a single device. The present invention lessens operator fatigue, the potential for confusion, incorrect order of operations, and reduces the number of hands used for operation of the syringe device.

In one embodiment, the present invention provides a syringe device for agitating and delivering a liquid medication to a patient. The syringe device includes an injecting member, a first syringe, a second syringe, and an elastic accumulator. The first syringe is configured to acquire the liquid medication and supply the liquid medication to the syringe device. The second syringe is in fluid communication with the injecting member and the first syringe. The second syringe is configured to receive the liquid medication from the first syringe and force the liquid medication to the injecting member for patient delivery. The accumulator is in fluid communication with the second syringe. The accumulator is biased to an empty position. The biased accumulator cooperates with the second syringe to agitate the liquid medication back and forth between the second syringe and the accumulator prior to patient delivery.

In another embodiment, the present invention provides a syringe device for agitating and delivering a liquid medication to a patient. The syringe device includes an injecting member, a first syringe, a second syringe, and an elastic accumulator. The first syringe is configured to acquire the liquid medication and supply the liquid medication to the syringe device. The second syringe is configured to fluidly communicate with the injecting member and the first syringe. The second syringe is further configured to receive the liquid medication from the first syringe and force the liquid medication to the injecting member for patient delivery. The accumulator is configured to fluidly communicate with the second syringe. The accumulator is further configured to receive a portion of the liquid medication. The accumulator is biased to an empty position. A first valve couples the first syringe to the second syringe and is selectively adjustable between a first position and a second position. In the first position, the first and second syringes are in fluid communication with each other. In the second position, the first and second syringes are not in fluid communication with each other.

A second valve proximal the first valve couples the accumulator to the second syringe and is selectively adjustable between first, second, and third positions. In the first position, the accumulator and the second syringe are in fluid communication with each other and the second valve is not in fluid communication with the first valve. In the second position, the accumulator and the second syringe are in fluid communication with each other and the second valve is in fluid communication with the first valve. In the third position, the accumulator and the second syringe are not in fluid communication with each other and the second valve is in fluid communication with the first valve. In this embodiment, the second syringe is in fluid communication with the injecting member when the first valve is in the second position and when the second valve is in the third position.

In another embodiment, the present invention provides a syringe device for agitating and delivering a liquid medication to a patient. The syringe device includes an injecting member, a first syringe, a second syringe, and an elastic accumulator. The first syringe is configured to acquire the liquid medication and supply the liquid medication to the syringe device. The first syringe includes a first barrel having a first plunger longitudinally slidable within the first barrel. The second syringe is configured to fluidly communicate with the injecting member and the first syringe. The second syringe is further configured to receive the liquid medication from the first syringe and force the liquid medication to the injecting member for patient delivery. The second syringe includes a second barrel and a second plunger longitudinally slidable within the second barrel. The accumulator is configured to fluidly communicate with the second syringe. The accumulator is biased to an empty position. The biased accumulator cooperates with the second syringe and includes a third barrel and a third plunger longitudinally slidable within the third barrel. The third plunger is biased to an empty position.

The first plunger of the first syringe forms the third barrel of the accumulator such that the accumulator is longitudinally slidable within the first syringe. A locking element is configured to prevent the accumulator from sliding within the first syringe when in a locked position. A valve couples the first syringe to the second syringe. The valve is selectively adjustable between a first position and a second position. In the first position, the first syringe and the accumulator are in fluid communication with the second syringe; and, the first syringe, the accumulator, and the second syringe are not in fluid communication with the injecting member. In the second position, the first syringe and the accumulator are not in fluid communication with the second syringe or the injecting member; and, the second syringe is in fluid communication with the injecting member.

In another example, the present invention provides a method of agitating and delivering a liquid medication to a patient. The method comprises providing a syringe device including an injecting member, a first syringe, a second syringe, and an elastic accumulator. The first syringe acquires the liquid medication and supplies the liquid medication to the syringe device. The second syringe is configured to receive the liquid medication from the first syringe and force the liquid medication to the injecting member for patient delivery. The accumulator is configured to receive a portion of the liquid medication and to agitate the liquid medication back and forth between the accumulator and the second syringe. The accumulator is biased to an empty position. The method further comprises transferring the liquid medication from the first syringe to the second syringe; shuttling the liquid medication back and forth between the second syringe and the accumulator; and transferring the liquid medication from the second syringe to the injecting member for patient delivery.

Further objects, features, and advantages of the present invention will become apparent from consideration of the following description and the appended claims when taken in connection with the accompanying drawings.

BRIEF DESCRIPTION OF THE DRAWINGS

FIGS. 1*a-d* are cross-sectional side views of a syringe device in accordance with an embodiment of the present invention;

FIGS. 2*a-d* are cross-sectional side views of a syringe device in accordance with another embodiment of the present invention;

DETAILED DESCRIPTION OF THE INVENTION

Figure 1A:
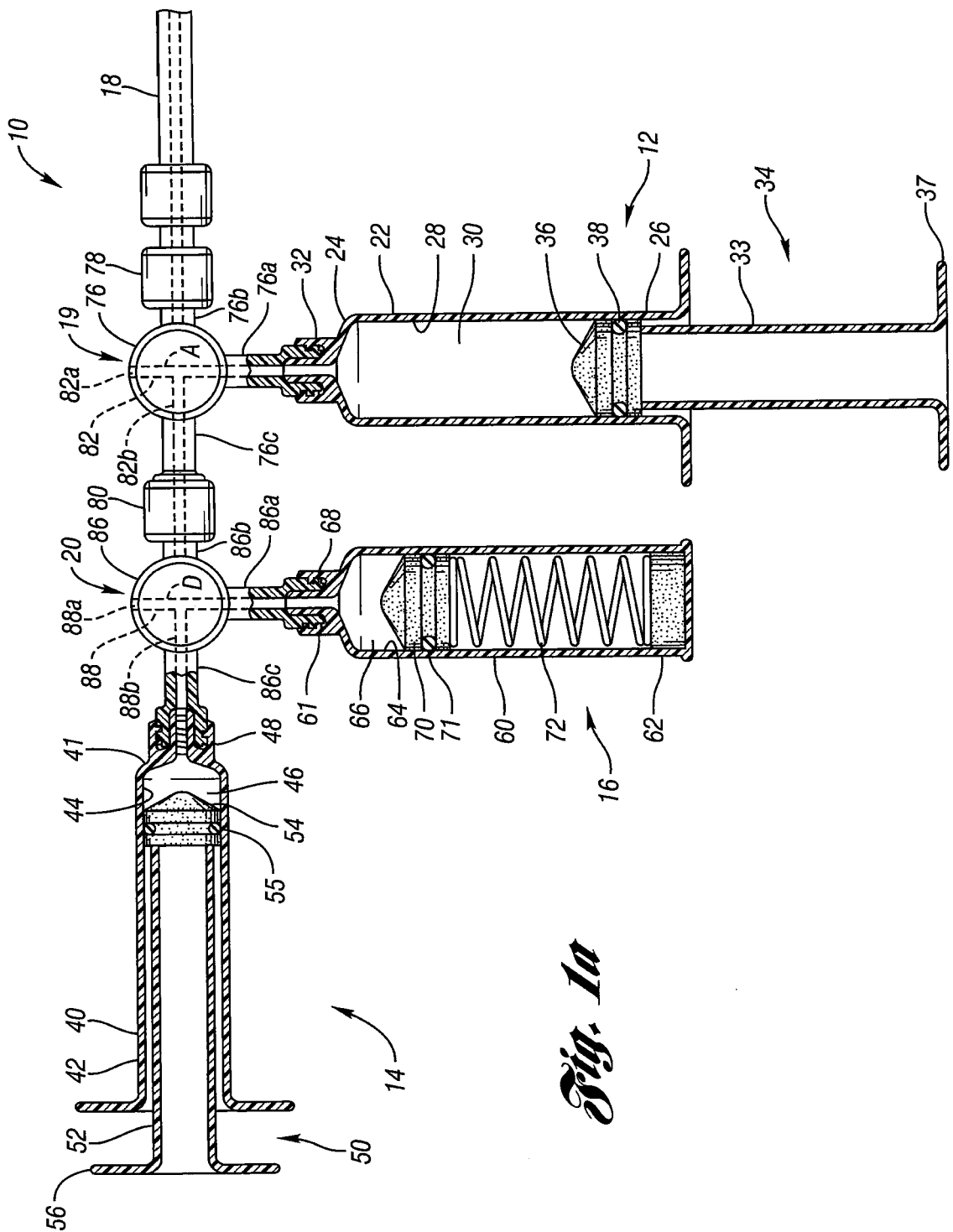

The present invention generally provides a syringe device for agitating and delivering liquid medications such as liquid embolic compositions. The syringe device may also be used for agitating and delivering other medications, especially those which comprise polymer particles. Embodiments of the present invention seek to overcome the problems associated with premature aggregation of a liquid embolic composition within a syringe or catheter before delivery to a vascular site. Embodiments of the present invention allow the operator to use one hand to agitate the liquid embolic composition to prevent premature aggregation as opposed to prior art embodiments which require the use of two hands to agitate the liquid embolic composition and prevent premature aggregation.

FIGS. 1*a-d* illustrate a syringe device 10 for agitating and delivering a liquid embolic composition in accordance with one embodiment of the present invention. As shown, the syringe device 10 includes a first syringe 12, a second syringe 14, an elastic accumulator 16, and a catheter 18, all of which are designed to be selectively fluidly coupled together via valves 19 and 20 so as to transfer the liquid embolic composition within the syringe device 10.

In this embodiment, the first syringe 12 includes a generally cylindrical barrel 22 having a distal end 24 and an opposing proximal end 26. The barrel 22 has an interior surface 28 bounding a chamber 30 configured to contain the liquid embolic composition. The barrel 22 may be made of any material suitable for holding a liquid embolic composition. In this embodiment, the first syringe 12 further includes a tubular tip 32 projecting from the distal end 24 and a plunger 34 comprising a plunger rod 33 having a first end inserted in the barrel 22 at the proximal end 26. A stopper or piston 36 arranged on the first end of the plunger rod 33 is longitudinally slidable with the plunger rod 33 within the chamber 30. The piston 36 comprises a seal member 38, such as an o-ring, to sealingly engage the interior surface 28 of the barrel 22 during actuation of the plunger 34. A second end of the plunger rod 33 includes a plunger handle 37 for actuating the plunger 34. The first syringe 12 preferably has a capacity of around ten to around twenty cubic centimeters. The capacity of the first syringe 12 may be less than around ten cubic centimeters or greater than around twenty cubic centimeters as long as the first syringe 12 is suitable for aspirating and containing the liquid embolic composition from an outside container and providing it to the syringe device 10.

In this embodiment, the second syringe 14 includes a barrel 40 having a distal end 41 and an opposing proximal end 42. The barrel 40 has an interior surface 44 bounding a chamber 46 configured to contain the liquid embolic composition. The barrel 40 may be made of any material suitable for holding a liquid embolic composition. In this embodiment, the second syringe 14 further includes a tubular tip 48 projecting from the distal end 41 and a plunger 50 comprising a plunger rod 52 having a first end inserted in the barrel 40 at the proximal end 42. A stopper or piston 54 arranged on the first end of the plunger rod 52 is longitudinally slidable with the plunger rod 52 within the chamber 46. The piston 54 comprises a seal member 55, such as an o-ring, to sealingly engage the interior surface 44 during actuation of the plunger 50. A second end of the plunger rod 52 includes a plunger handle 56 for actuating the plunger 50. The second syringe 14 is a smaller, high pressure syringe having a capacity of around one to around three cubic centimeters. The capacity of the second syringe 14 may be greater than around three cubic centimeters as long as the second syringe 14 is suitable for agitating the liquid embolic composition back and forth with the accumulator 16 and forcing it to the catheter 18 for patient delivery.

In this embodiment, the accumulator 16 is in the form of a pseudo-syringe and includes a barrel 60 having a distal end 61 and an opposing proximal end 62. The barrel 60 has an interior surface 64 bounding a chamber 66 configured to contain the liquid embolic composition. The barrel 60 may be made of any material suitable for holding a liquid embolic composition. The accumulator 16 further includes a tubular tip 68 projecting from the distal end 61 and a stopper or piston 70 slidably disposed within the chamber 66. The piston 70 is biased towards the distal end 61 (i.e., an empty position) by a biasing member, such as a spring 72 or any other suitable biasing member (foam, gas, balloon, elastomer, electromagnetic field, gravity, etc.). The piston 70 comprises a seal member 71, such as an o-ring, to sealingly engage the interior surface 64 as the piston 70 slides within the chamber 66. The accumulator 16 preferably has a capacity of around one to around three cubic centimeters (approximately equal to that of the second syringe 14). The capacity of the accumulator 16 may be greater than around three cubic centimeters as long as the accumulator 16 is suitable for agitating the liquid embolic composition back and forth with the second syringe 14.

Figure 4:
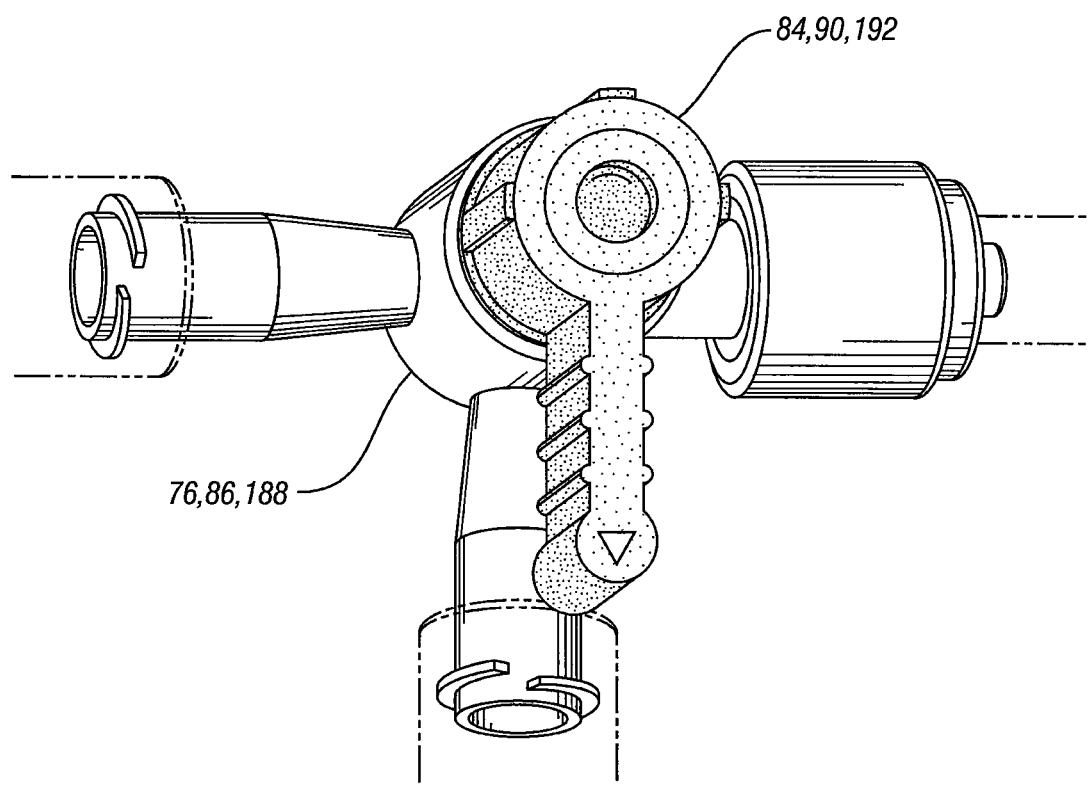
FIG. 4 is a top view of a valve of a syringe device in accordance with an embodiment of the present invention.

In this embodiment, the first syringe 12 has a Luer fitting, which is lockable to the three-way valve 19 by a screw thread at the tip 32 of the first syringe 12. The valve 19 has an outer plastic cylindrical collar 76 having a first projecting, partially threaded, tubular port 76a, to which the tip 32 of the first syringe 12 is screwed, securing a fluid-tight seal. The collar 76 also has a second, projecting, tubular port 76b, which is arranged at 90 degrees to the port 76a, and is configured to retain the injecting member 18, such as a catheter or a sterile needle, by means of a threaded collar 78. The collar 76 also has a third, projecting, tubular port 76c, which is arranged at 90 degrees to the port 76a and opposite the port 76b, forming a T-shaped arrangement. The port 76c connects to the valve 20 by means of a threaded collar 80 or any other suitable connector. The valve 19 has an inner plastic cylindrical valve member 82, retained within the collar 76 and having a bore 82a extending along a diameter. The valve member 82 also has a bore 82b, which extends along half a diameter and thus intersects at a right angle the bore 82a, with which it is in fluid communication, forming a T-shaped arrangement. The bores 82a, b preferably have an internal diameter of the order of about 1 mm. The valve member 82 has an integral arm 84, illustrated in FIG. 4, which projects beyond the collar 76 and serves as a manually rotatable means configured to enable rotation of the valve member 82 and to indicate the orientation of the bores 82a, b therein.

In a preferred embodiment, the valve member 82 is rotatable into various positions. It is positionable so that the ports 76a and 76c are in fluid communication with each other and the port 76b is sealed off from each of them (Position A, shown in FIGS. 1a and 1b). The valve member 82 is rotatable from that position through 90 degrees so that the ports 76b and 76c are in fluid communication with each other via the bore 82a only and the port 76a is sealed off from each of them. (Position B, shown in FIG. 1c). The valve member 82 may also be rotatable into various intermediate positions in which the ends of the bores 82a, b do not coincide with any of the ports 76a, b, c, so that each of the ports is sealed off from each of the other ports.

In this embodiment, the second syringe 14 has a Luer fitting, which is lockable to the three-way valve 20 by a screw thread at the tip 48 of the second syringe 14. The accumulator 16 has a Luer fitting, which is lockable to the valve 20 by a screw thread at the tip 68 of the accumulator 16. The valve 20 has an outer plastic cylindrical collar 86 having a first, projecting, partially threaded, tubular port 86a, to which the tip 68 of the accumulator 16 is screwed, securing a fluid-tight seal. The collar 86 also has a second, projecting, tubular port 86b, which is arranged at 90 degrees to port 86a, and connects to the valve 19 by means of the threaded collar 80. The collar 86 also has a third, projecting, partially threaded, tubular port 86c, which is arranged at 90 degrees to the port 86a and opposite the port 86b, forming a T-shaped arrangement. The tip 48 of the second syringe 14 is screwed to the port 86c, securing a fluid-tight seal. The valve 20 has an inner plastic cylindrical valve member 88, retained within the collar 86 and having a bore 88a extending along a diameter. The valve member 88 also has a bore 88b, which extends along half a diameter and thus intersects at a right angle the bore 88a, with which it is in communication, forming a T-shaped arrangement. The bores 88a, b have an internal diameter of the order of about 1 mm. The valve member 88 has an integral arm 90, illustrated in FIG. 4, which projects beyond the collar 86 and serves as a manually rotatable means configured to enable rotation of the valve member 88 and to indicate the orientation of the bores 88a, b therein.

In a preferred embodiment, the valve member 88 is rotatable into various positions. It is positionable so that the ports 88a, b are in communication with the ports 86a, b, c, which are hence in communication with each other (Position C, shown in FIG. 1b). It is rotatable from that position through 90 degrees so that the ports 86a and 86c are in communication with each other and the port 86b is sealed off from each of them (Position D, shown in FIGS. 1a and 1c). It is rotatable by a further 90 degrees so that the ports 86b and 86c are in communication with each other via the bore 88a only and the port 86a is sealed off from each of them. (Position E, shown in FIG. 1d). The valve member 88 is also rotatable into various intermediate positions in which the ends of the bores 88a, b do not coincide with any of the ports 86a, b, c, so that each of the ports is sealed off from each of the other ports.

In this embodiment, the first syringe 12 provides the liquid embolic composition to the syringe device 10 which includes acquiring the liquid embolic composition from an outside container (not shown). For example, in use, the first syringe 12 is detached from the syringe device 10, aspirates the liquid embolic composition from an outside container, and is then loaded, or reattached, to the syringe device 10 to provide the liquid embolic composition to the second syringe 14. As illustrated in FIG. 1a, the valve 19 is in position A and the valve 20 is in position D when the first syringe 12 is reattached to the syringe device 10. The port 76b is sealed off so that the liquid embolic composition cannot enter the catheter 18 from the first syringe 12 and the port 86b is sealed off so that the liquid embolic composition cannot yet enter the second syringe 14. The plunger 50 of the second syringe 14 is initially positioned towards the distal end 41, defining an empty position.

Figure 1B:
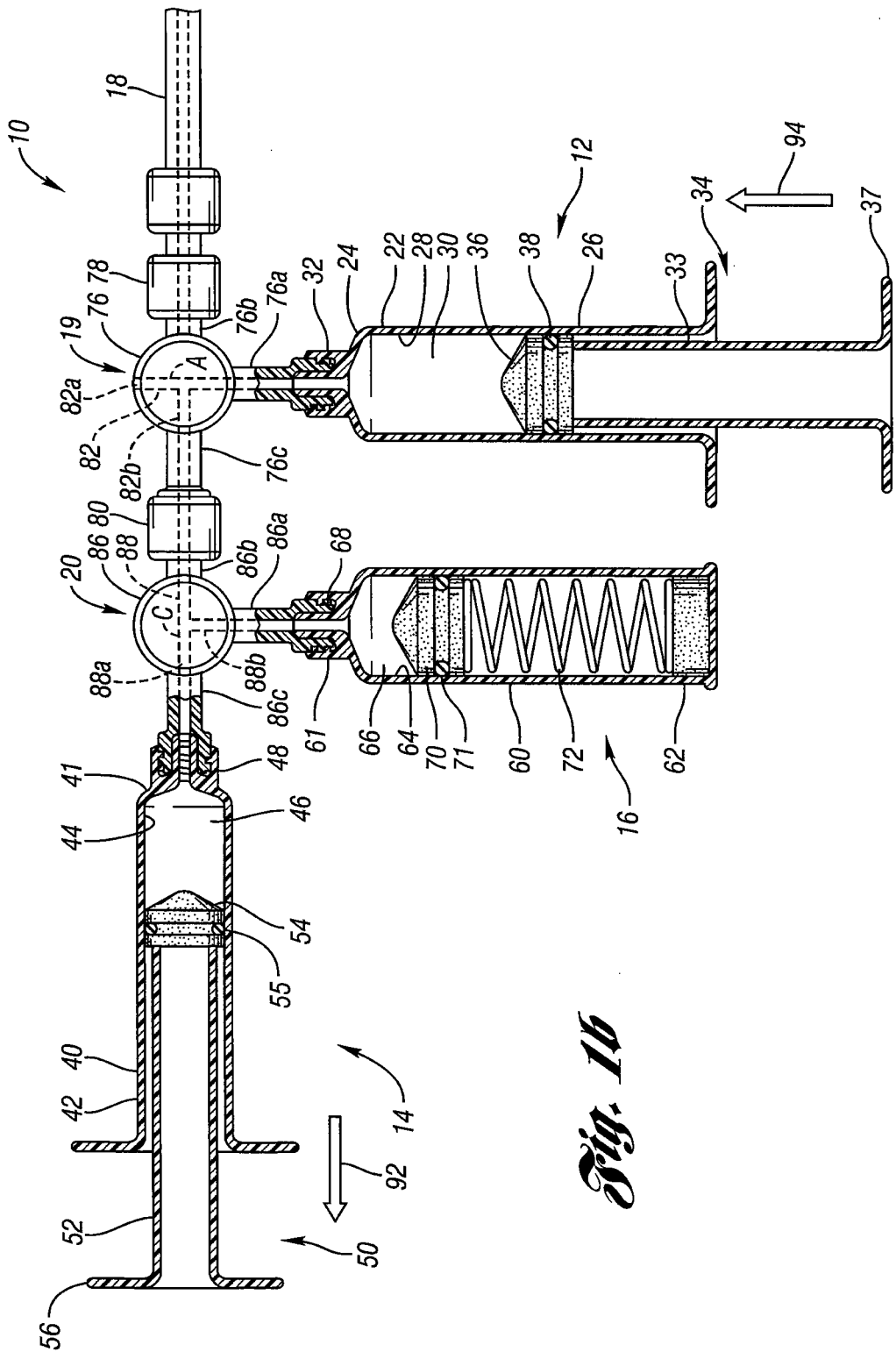
Figure 1C:
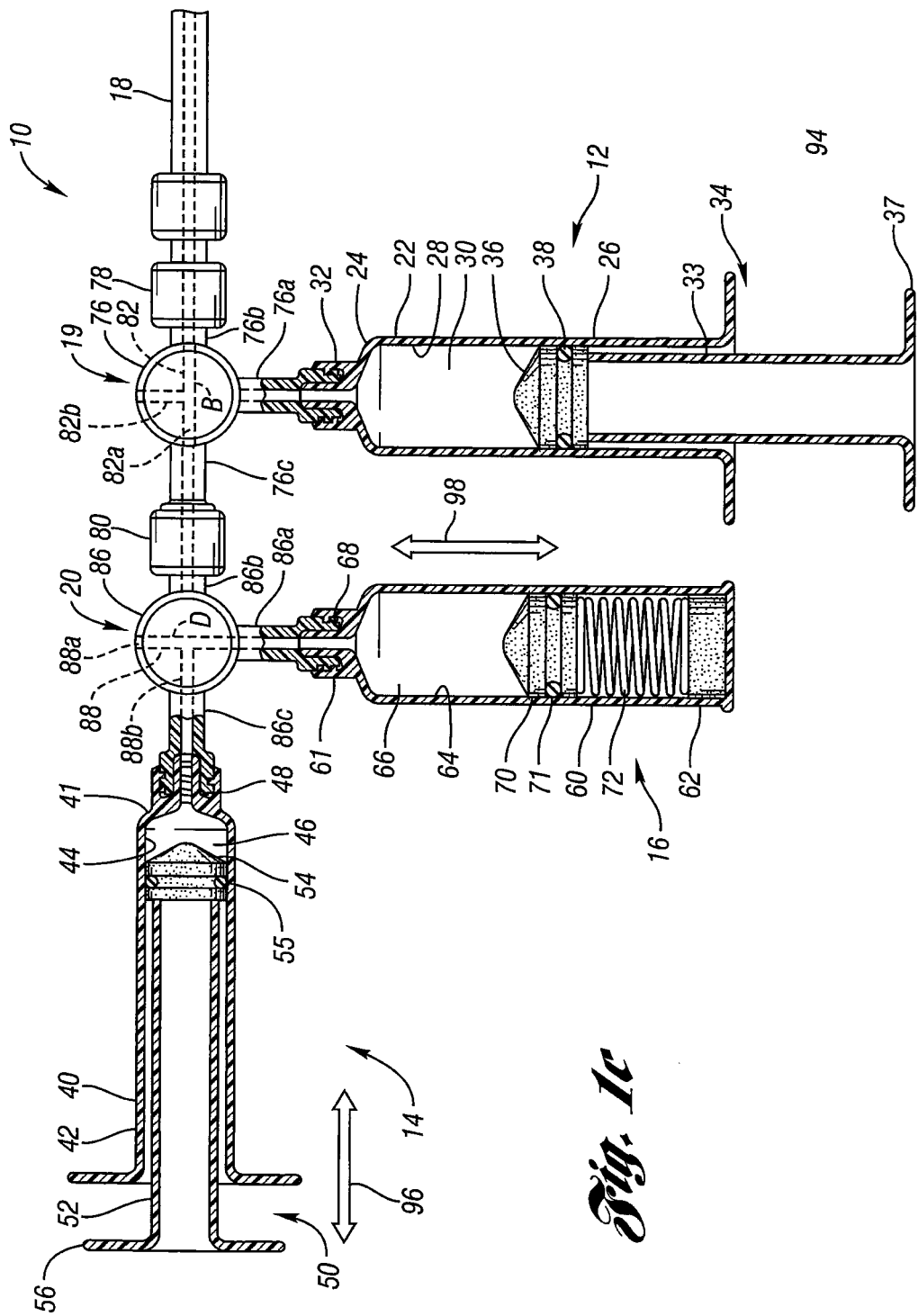
Figure 1B:
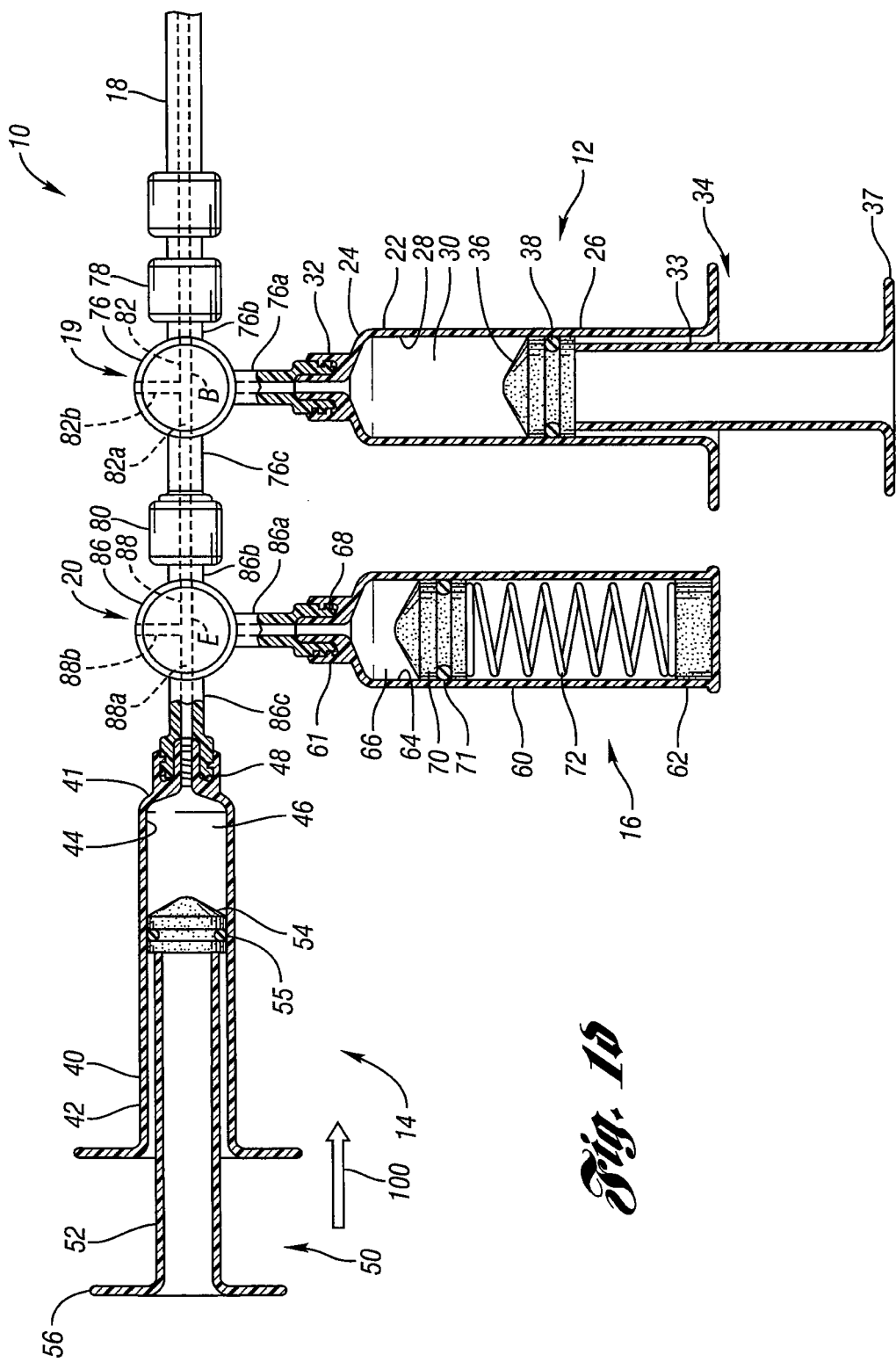

The liquid embolic composition is transferred to the second syringe 14 by actuating the plunger 50 to measure out a predetermined volume of the liquid embolic composition. As illustrated in FIG. 1b, the plunger 50 is retracted to draw the liquid embolic composition into the barrel 40. The actuation of the plunger 50 in the direction of arrow 92 moves the piston 54 from the distal end 41 towards the proximal end 42, indicative of an increase in volume. As the predetermined volume of liquid embolic composition is displaced from the first syringe 12 and drawn into the second syringe 14, the piston 36 of the first syringe 12 moves in the direction of arrow 94, from the proximal end 26 towards the distal end 24. Both of the pistons 54 and 36 are moved a particular distance associated with the predetermined volume of liquid embolic composition displaced from the first syringe 12 and drawn into the second syringe 14.

Preferably, during transfer of the liquid embolic composition from the first syringe 12 into the second syringe 14, the valve 20 is in position C and the valve 19 is in position A, which selectively places the port 86a in fluid communication with the ports 86b and 86c. Thus, the accumulator 16 is in fluid communication with the first syringe 12 and the second syringe 14. The spring 72 of the accumulator 16 biases the piston 70 towards the distal end 61, defining an empty position. Therefore, when the plunger 50 is actuated to draw in a predetermined volume of the liquid embolic composition, the liquid embolic composition travels the path of least resistance from the first syringe 12 directly to the second syringe 14, rather than entering the accumulator 16. Alternatively, the valve 20 may be in a position where port 86a is not in fluid communication with ports 86b and 86c, but wherein the second syringe 14 is in fluid communication with the first syringe 12.

Next, the valve 20 is moved to position D, putting the accumulator 16 and the second syringe 14 in exclusive fluid communication with one another. The liquid embolic composition is agitated back and forth between the second syringe 14 and the accumulator 16 to prevent premature precipitation of the liquid embolic composition. The port 86b is sealed off and the predetermined volume of the liquid embolic composition is confined to the path between the second syringe 14 and the accumulator 16, defined by the ports 86a and 86c. Since the port 86b is sealed off during agitation, the positioning of the valve 19 is not important with respect to its communication with the valve 20. However, the valve 19 should be positioned so as to prevent the liquid embolic composition contained within the first syringe 12 from being transferred to the catheter 18. For example, the valve 19 may be rotated to position B so that the port 76a is sealed off and the liquid embolic composition within the first syringe 12 is confined within the chamber 30 of the first syringe 12.

During agitation, the plunger 50 of the second syringe 14 is actuated. As the plunger 50 is selectively advanced towards the distal end 41 of the barrel 40 (i.e., an empty position), the pressure applied to the plunger 50 provides a force which pushes the predetermined volume of liquid embolic composition out of the second syringe 14, through the port 86c and the bores 88b and 88a, further through the port 86a, and into the accumulator 16. The liquid embolic composition enters the chamber 66 of the accumulator 16 and forces the biased piston 70 towards the proximal end 62 of the accumulator 16, compressing the spring 72 against its spring seat. As the pressure applied to the plunger 50 of the second syringe 14 is released, the accumulator 16 passively returns the liquid embolic composition to the second syringe 14 due to the force which advances the biased piston 70 towards the distal end 61 of the third barrel 60 (i.e., an empty position). The liquid embolic composition travels back through the port 86a and the bores 88a and 88b, further back through the port 86c, and back into the second syringe 14, causing the plunger 50 to retract towards the proximal end 42 of the barrel 40. The manipulation of the plunger 50 towards the distal end 41 cooperates with the biasing spring 72 of the accumulator 16, to agitate the liquid embolic composition back and forth between the second syringe 14 and the accumulator 16. Thus, the plunger 50 moves back and forth within the chamber 46 in the direction of arrow 96 and the biased piston 70 moves back and forth within the chamber 66 in the direction of arrow 98.

Actuation of the plunger 50 of the second syringe 14 may be repeated a number of times to sufficiently agitate the liquid embolic composition and prevent premature precipitation. The syringe device 10 allows the use of one hand to agitate and deliver the liquid embolic composition. Rather than requiring two hands to actuate two plungers of two syringes for agitating back and forth between the two syringes, the addition of the accumulator 16, having a biased piston 70, eliminates the need of a second hand to actuate a second plunger of a second syringe. Accordingly, manual actuation of the plunger 50, in combination with the biased accumulator 16, cooperate to agitate the liquid embolic composition within the syringe device 10, requiring the use of only one hand.

Next, the valve 19 is put in position B and the valve 20 is put in position E, illustrated in FIG. 1d. The ports 86a and 76a are sealed off, preventing the liquid embolic composition from entering the accumulator 16 and the first syringe 12, respectively. The liquid embolic composition is forced from the second syringe 14 to the catheter 18 for injection into a vascular site. As the plunger 50 is selectively advanced towards the distal end 41 in the direction of arrow 100 (i.e., an empty position), the pressure applied to the plunger 50 provides a force which pushes the predetermined volume of liquid embolic composition out of the second syringe 14 and into the catheter 18. Due to the positioning of the valves 19, 20, the liquid embolic composition travels from the second syringe 14, through the port 86c, the bore 88a, the port 86b, the collar 80, the port 76c, the bore 82a, the port 76b, the collar 78, and into the catheter 18 for patient delivery.

In one embodiment, the second syringe 14 may include a feature, such as an adjustable detent, or an escapement, configured to limit the travel of the stroke of the plunger 50 within the barrel 40 to allow a selectable or pre-selected fraction of the capacity of the second syringe 14 to be delivered to the catheter 18 for patient delivery. For example, if the second syringe 14 has a capacity of around three cubic centimeters, the adjustable detent may allow a one cubic centimeter bolus of the liquid embolic composition to be administered three successive times before the second syringe 14 will need to aspirate another load of the liquid embolic composition.

FIGS. 2a-e illustrate a syringe device 110 for agitating and delivering a liquid embolic composition in accordance with a second embodiment of the present invention. As shown, the syringe device 110 includes a first syringe 112, an accumulator 114 disposed within the first syringe 112, a second syringe 116, and an injecting member, such as a catheter 118, all of which are designed to be selectively fluidly coupled together via a three-way valve 120 so as to transfer the liquid embolic composition within the syringe device 110.

In this embodiment, the first syringe 112 includes a generally cylindrical barrel 122 having a distal end 124 and an opposing proximal end 126. The barrel 122 has an interior surface 128 bounding a chamber 130 configured to contain the liquid embolic composition. The barrel 122 may be made of any material suitable for holding a liquid embolic composition. The first syringe 112 further includes a tubular tip 132 projecting from the distal end 124 and a plunger 134 including a hollow plunger rod 136 having a first end inserted in the barrel 122 at the proximal end 126. A stopper or piston 138 arranged on the first end of the plunger rod 136 is longitudinally slidable with the plunger rod 136 within the chamber 130. The piston 138 comprises a seal member 140, such as an o-ring, to sealingly engage the interior surface 128 of the barrel 122 during actuation of the plunger 134. A second end of the plunger rod 136 includes a plunger handle 137. The first syringe 112 has a capacity of around ten to around twenty cubic centimeters. The capacity of the first syringe 112 may be less than around ten cubic centimeters or greater than around twenty cubic centimeters as long as the first syringe 112 is suitable for aspirating and containing the liquid embolic composition from an outside container and providing it to the syringe device 110.

In this embodiment, the plunger rod 136 forms the barrel of the accumulator 114. The barrel 136 includes a distal end 142 and an opposing proximal end 144. Preferably, the barrel 136 has a partially threaded outer surface 146 and an interior surface 148 bounding a chamber 150 configured to contain the liquid embolic composition. The chamber 150 is in fluid communication with the chamber 130 through a channel 151 formed in the piston 138. The accumulator 114 includes a plunger 152 including a plunger rod 153 having a first end 154 inserted in the barrel 136 at the proximal end 144. A stopper or piston 156 arranged on the plunger rod 153 is longitudinally slidable with the plunger rod 153 within the chamber 150. The piston 156 comprises a seal member 158, such as an o-ring, to sealing engage the interior surface 148 of the barrel 136. The piston 156 is biased towards the distal end 142 (i.e., an empty position) by a biasing member, such as a spring 160 or any other suitable biasing member. In the biased position, the first end 154 of the plunger rod 153 is proximate the distal end 142 of the barrel 136 and the second end 155 of the plunger rod 153 is proximate the proximal end 144 of the barrel 136. The accumulator 114 within the first syringe 112 is in the form of a high pressure syringe, having a capacity of around one to around three cubic centimeters. The capacity of the accumulator 114 may be greater than around three cubic centimeters as long as the accumulator 114 is suitable for agitating the liquid embolic composition back and forth with the third syringe 116.

In this embodiment, the syringe device 110 further includes a locking element 162 configured to lock the plunger rod 136 in place within the first syringe 112. As shown in FIGS. 2a-e and FIG. 3, the locking element 162 includes a cam lever 164 which cooperates with a thread member 166 which intersects the barrel 122 of the first syringe 112 to engage the threaded outer surface 146 of the plunger rod 136 so as to lock the plunger rod 136 in place within the first syringe 112. In this embodiment, the locking element 162 prevents linear, or longitudinal, movement of the plunger rod 136 within the first syringe 112. Any other suitable biasing member or locking element may be used to prevent longitudinal movement of the second syringe 114 within the first syringe 112.

In this embodiment, the second syringe 116 includes a barrel 168 having a distal end 170 and an opposing proximal end 172. The barrel 168 has an interior surface 174 bounding a chamber 176 configured to contain the liquid embolic composition. The barrel 168 may be made of any material suitable for holding a liquid embolic composition. In this embodiment, the second syringe 116 further includes a tubular tip 178 projecting from the distal end 170 and a plunger 180 comprising a plunger rod 182 having a first end inserted in the barrel 168 at the proximal end 172. A stopper or piston 184 arranged on the plunger rod 182 is longitudinally slidable with the plunger rod 182 within the chamber 176. The piston 184 comprises a seal member 186, such as an o-ring, to sealingly engage the interior surface 174 of the barrel 168 during actuation of the plunger 180. A second end of the plunger rod 182 includes a plunger handle 183 for actuating the plunger 180. The second syringe 116 has a capacity of around one to around three cubic centimeters. The capacity of the second syringe 116 may be greater than around three cubic centimeters as long as the second syringe 116 is suitable for agitating the liquid embolic composition back and forth with the accumulator 114 within the first syringe 112 and transferring it to the catheter 18 for patient delivery.

In this embodiment, the first syringe 112 has a Luer fitting, which is lockable to the valve 120 by a screw thread at the tip 132 of the first syringe 112. The valve 120 has an outer plastic cylindrical collar 188 having a first projecting, partially threaded, tubular port 188a, to which the tip 132 of the first syringe 112 is screwed, securing a liquid-tight seal. The collar 188 also has a second, projecting, tubular port 188b, which is arranged at 90 degrees to the port 188a, and is configured to retain a catheter 118 or a sterile needle, by means of a threaded collar 189. The collar 188 also has a third, projecting, tubular port 188c, which is arranged at 90 degrees to the port 188b and opposite the port 188b, forming a T-shaped arrangement. The tip 178 of the third syringe 116 is screwed to the port 188c, securing a liquid-tight seal.

In this embodiment, the valve 120 has an inner plastic cylindrical valve member 190, retained within the collar 188 and having a bore 190a extending along a diameter. The valve member 190 also has a bore 190b, which extends along half a diameter and thus intersects at a right angle the bore 190a, with which it is in communication, forming a T-shaped arrangement. The bores 190a, b have an internal diameter of the order of about 1 mm. The valve member 190 has an integral arm 192, illustrated in FIG. 4, which projects beyond the collar 188 and serves as a manually rotatable means configured to enable rotation of the valve member 190 and to indicate the orientation of the bores 190a, b therein. The valve member 190 is rotatable into various positions. It is positionable so that the ports 188a and 188c are in communication with each other and the port 188b is sealed off from each of them (Position F, shown in FIGS. 2a-c). It is rotatable from that position through 90 degrees so that the ports 188b and 188c are in communication with each other via the bore 190a only and the port 188a is sealed off from each of them. (Position G, shown in FIG. 2d). The valve member 190 is also rotatable into various intermediate positions in which the ends of the bores 190a, b do not coincide with any of the ports 188a, b, c, so that each of the ports is sealed off from each of the other ports.

Figure 2A:
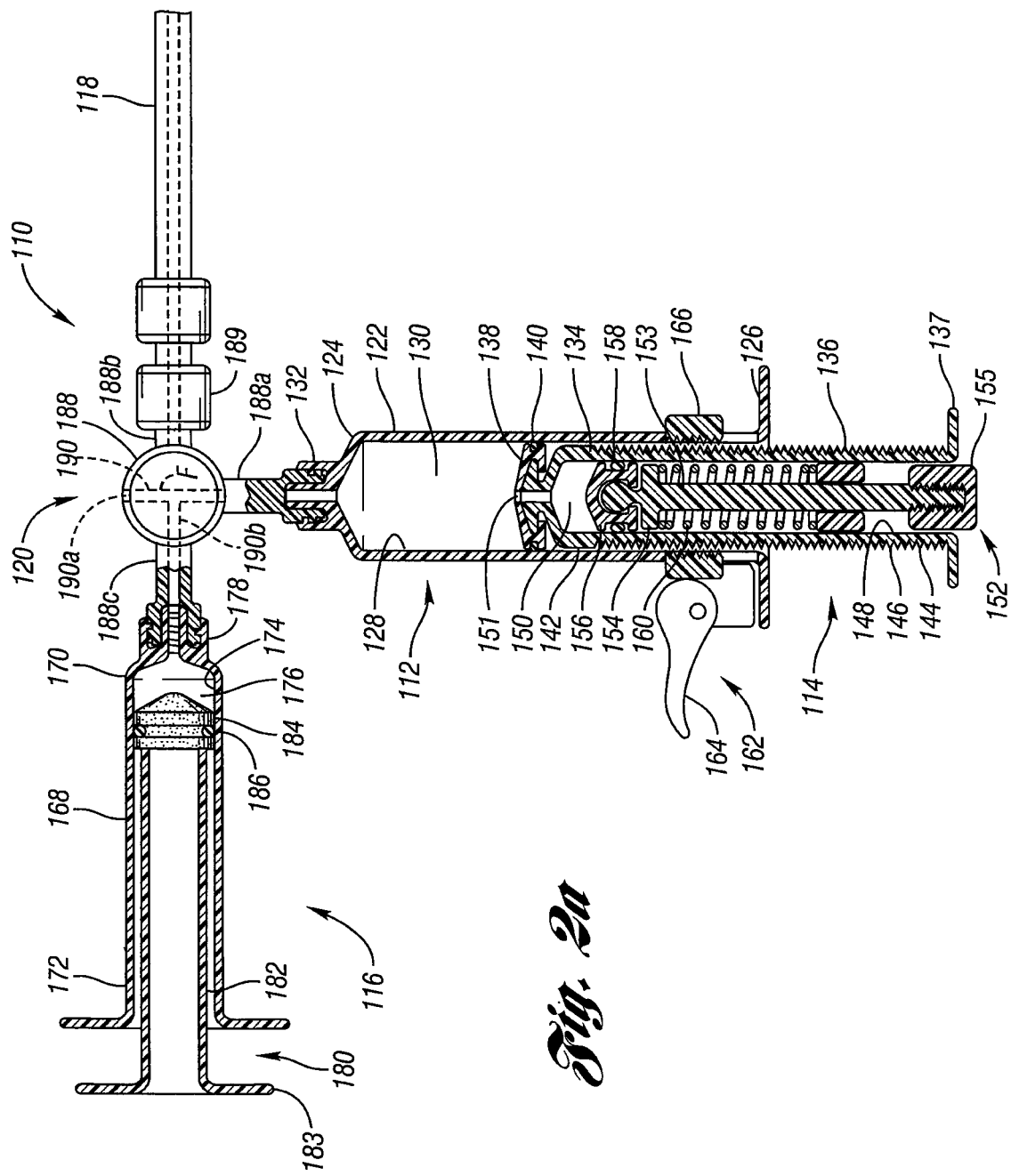

In this embodiment, the first syringe 112 provides the liquid embolic composition to the syringe device 110 which includes acquiring the liquid embolic composition from an outside container (not shown). For example, in use, the first syringe 112 is detached from the syringe device 110 to aspirate the liquid embolic composition from an outside container and is then loaded, or reattached, to the syringe device 110 to provide the liquid embolic composition to the second syringe 116. As illustrated in FIG. 2a, the valve 120 is in position F when the first syringe 112 is reattached to the syringe device 110. The port 188b is sealed off so that the liquid embolic composition cannot enter the catheter 118 from the first syringe 112. The plunger 180 of the second syringe 116 is initially positioned towards the distal end 170, defining an empty position.

Figure 2B:
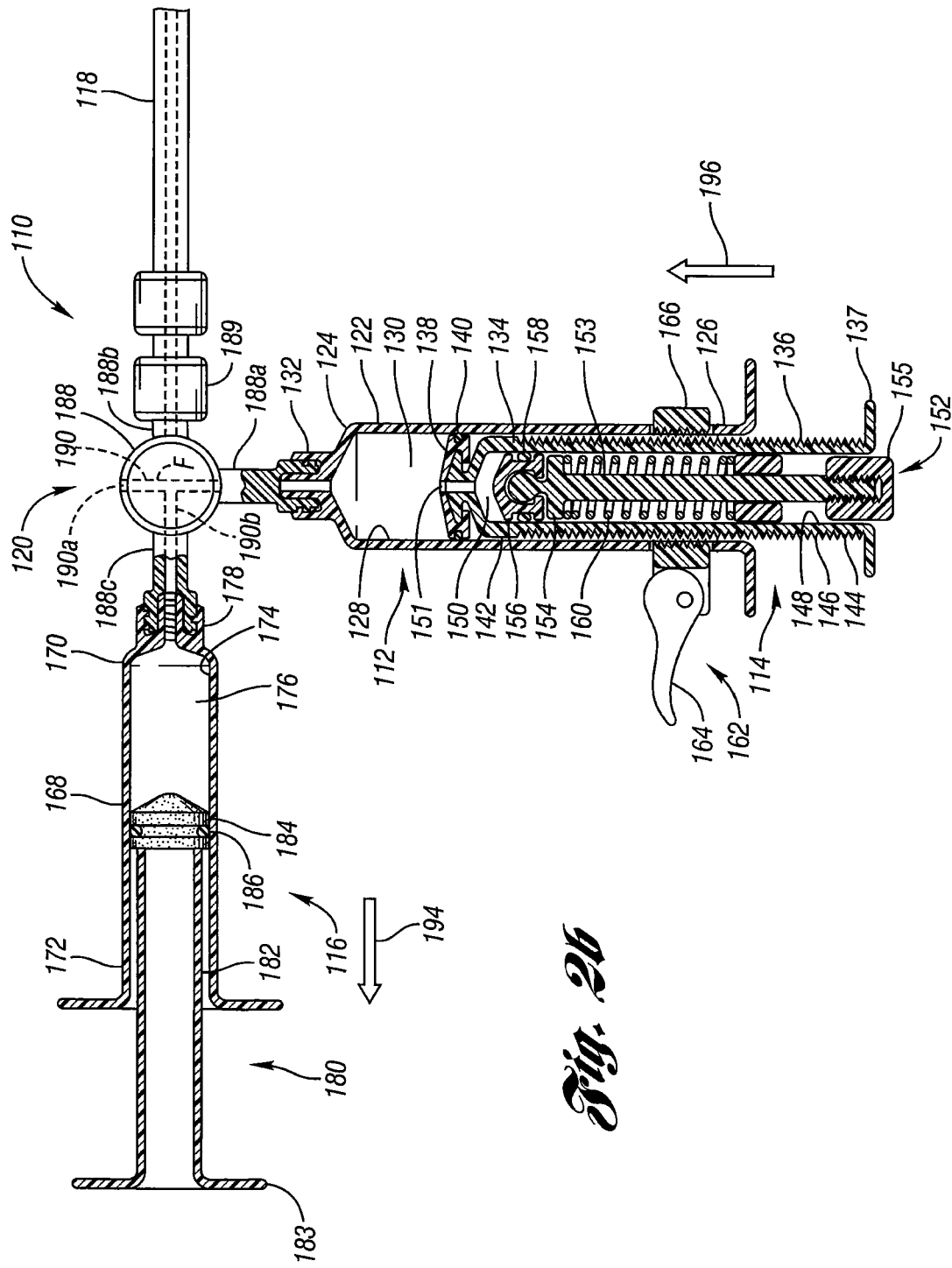

The liquid embolic composition is transferred into the second syringe 116 by actuating the plunger 180 to measure out a predetermined volume of the liquid embolic composition. As illustrated in FIG. 2b, the plunger 180 is retracted to draw the liquid embolic composition into the barrel 168. The actuation of the plunger 180 in the direction of arrow 194 moves the piston 184 from the distal end 170 towards the proximal end 172. As the predetermined volume of liquid embolic composition is displaced from the first syringe 112 and drawn into the second syringe 116, the piston 138 of the first syringe 112 moves in the direction of arrow 196, from the proximal end 126 towards the distal end 124. Both of the pistons 138 and 184 are moved a particular distance associated with the predetermined volume of liquid embolic composition displaced from the first syringe 112 and drawn into the second syringe 116.

During transfer of the liquid embolic composition from the first syringe 112 into the second syringe 116, the valve 120 is in position F, which selectively places the port 188a in fluid communication with the port 188c. Thus, the first syringe 112 is in fluid communication with the second syringe 116. Since the accumulator 114 within the first syringe 112 is biased towards the distal end 142 (i.e., an empty position), the liquid embolic composition remains within the chamber 130 of the first syringe 112 and does not enter the chamber 150 of the accumulator 114.

Figure 2C:
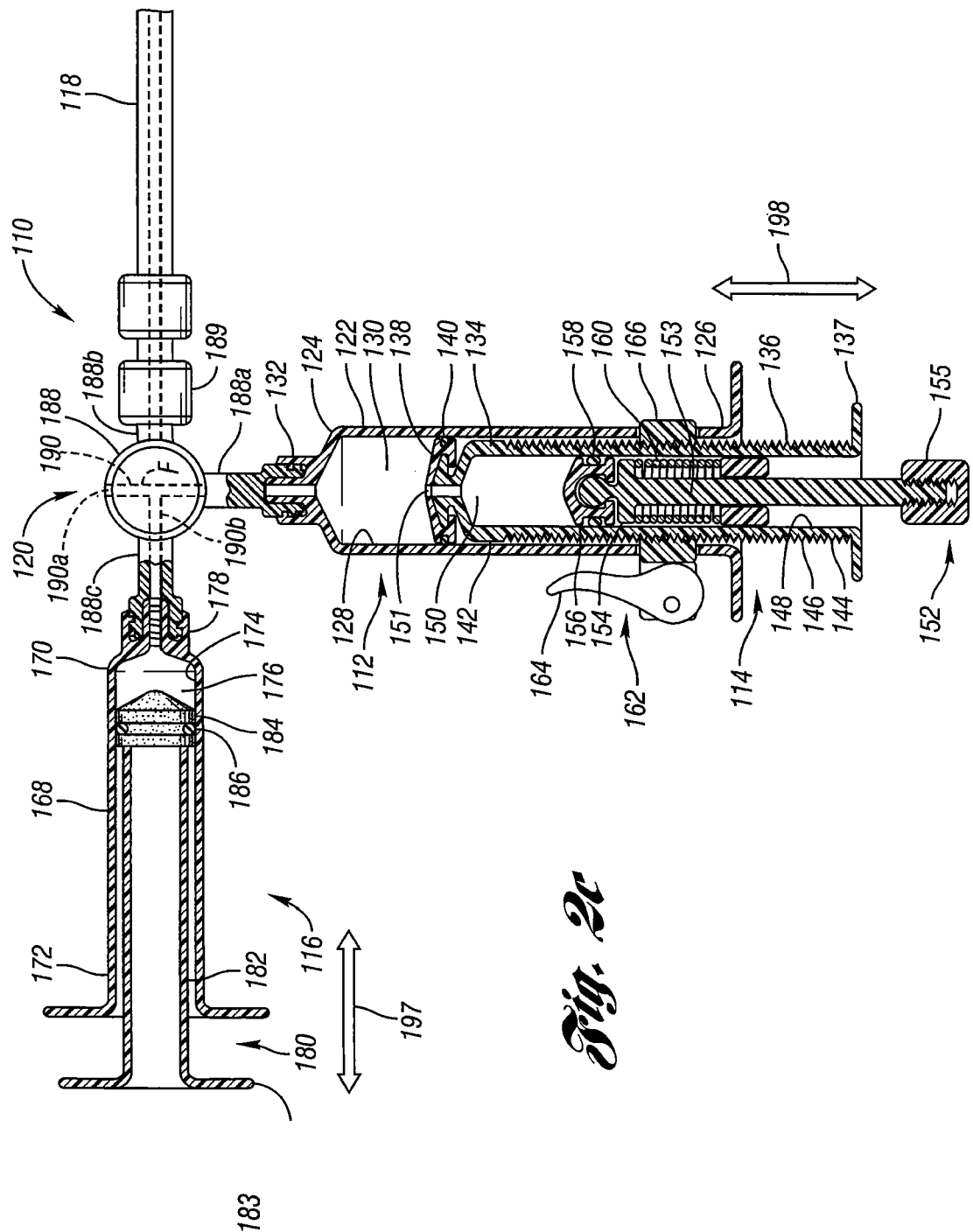
Figure 2E:
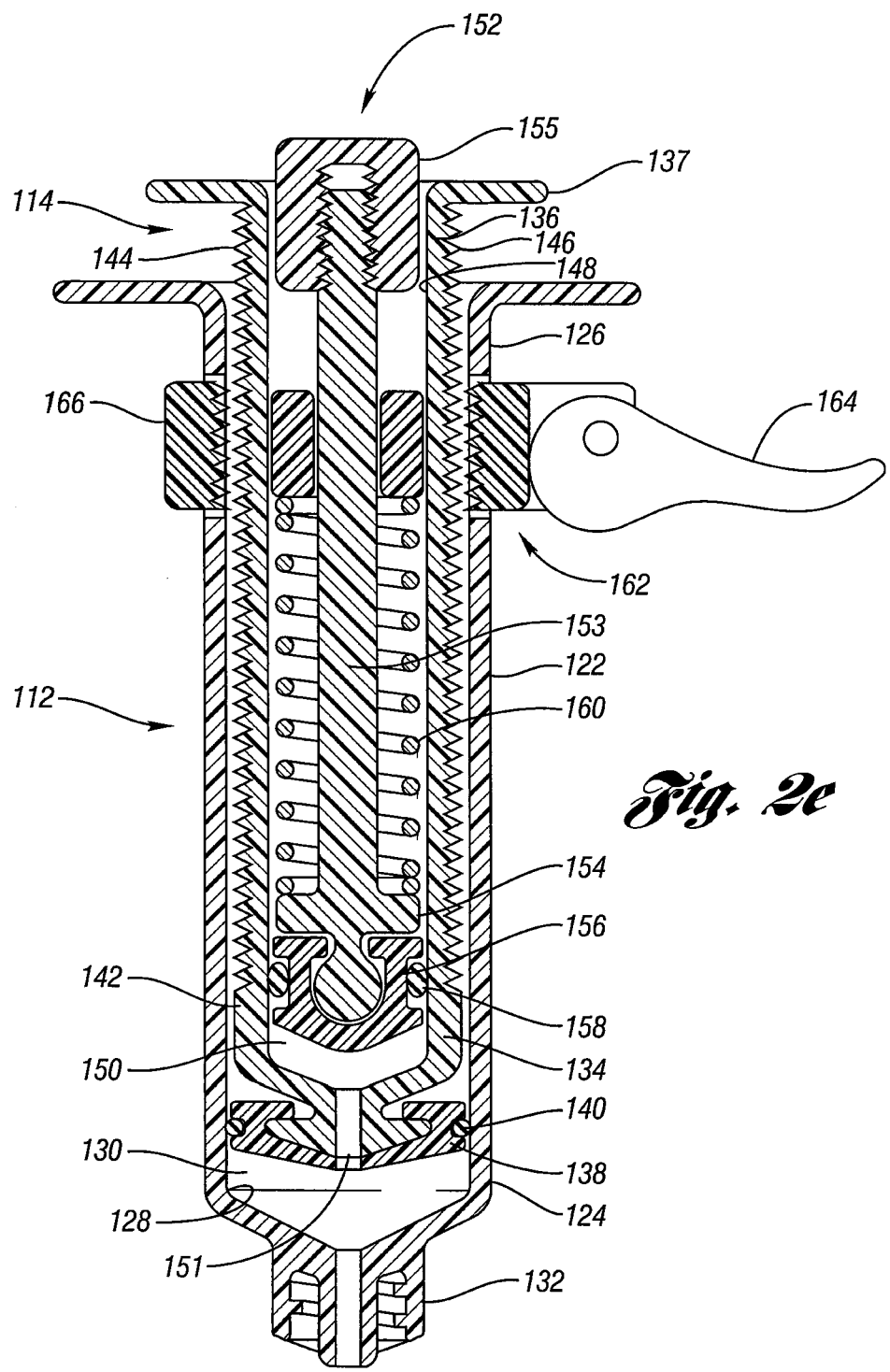
FIG. 2*e* is an expanded cross-sectional side view of a first syringe of the embodiment of FIGS. 2*a-d*.

The liquid embolic composition is agitated back and forth between the second syringe 116 and the accumulator 114 within the first syringe 112 to prevent premature precipitation of the liquid embolic composition. Agitation occurs when the valve 120 is in position F and when the locking element 162 is engaged in the locked position, as shown in FIG. 2c. The port 188b is sealed off and the predetermined volume of the liquid embolic composition is confined to the path between the second syringe 116 and the accumulator 114 within the first syringe 112, defined by the ports 188a and 188c. In the locked position, illustrated in FIGS. 2c and 2d, the cam lever 164 cooperates with the threaded member 166 to lock the barrel 136 of the second syringe 114 in place within the first syringe 112, thereby preventing longitudinal movement of the plunger 136 within the first syringe 112. The locking element 162 does not prevent rotational movement. For example, a slight rotation of the plunger/barrel 136 may be necessary to maneuver and release a small amount of trapped air within the chamber 130.

During agitation, the plunger 180 of the second syringe 116 is actuated. As the plunger 180 is selectively advanced towards the distal end 170 (i.e., an empty position), the pressure applied to the plunger 180 provides a force which pushes the predetermined volume of liquid embolic composition out of the second syringe 116, through the port 188c and the bores 190b and 190a, further through the port 188a, and into the first syringe 112. The liquid embolic composition enters the chamber 130 of the first syringe 112. The force of the liquid embolic composition entering the first syringe 112 would normally push the piston 138, and thus the barrel 136, of the accumulator 114 towards the proximal end 126. However, the locking element 162 prevents longitudinal movement of the barrel 136 within the first syringe 112. Consequently, the liquid embolic composition enters the chamber 150 of the accumulator 114 through the channel 151 of the piston 138 and forces the biased piston 156 towards the proximal end 144 of the accumulator 114, compressing the spring 160 against its spring seat. As the pressure applied to the plunger 180 of the second syringe 116 is released, the accumulator 114 passively returns the liquid embolic composition to the second syringe 116 due to the force which advances the biased piston 156 towards the distal end 142 of the second barrel 136. The liquid embolic composition travels back through the channel 151 to the chamber 130 of the first syringe 112, through the port 188a and the bores 190a and 190b, further back through the port 188c, and back into the second syringe 116, causing the plunger 180 to retract towards the proximal end 172 of the third barrel 168. The manipulation of the plunger 180 towards the distal end 170 cooperates with the locking element 162 and the biasing spring 160 of the accumulator 114 to agitate the liquid embolic composition back and forth between the second syringe 116 and the accumulator 114 within the first syringe 112. Thus, the plunger 180 moves back and forth within the chamber 176 in the direction of arrow 197 and the biased piston 156 moves back and forth within the chamber 150 in the direction of arrow 198.

Actuation of the plunger 180 of the second syringe 116 may be repeated a number of times to sufficiently agitate the liquid embolic composition and prevent premature precipitation. The syringe device 110 allows the use of one hand to agitate and deliver the liquid embolic composition. Rather than requiring two hands to actuate two plungers of two syringes for mixing back and forth between the two syringes, the accumulator 114 within the first syringe 112 and the biased piston 156 eliminate the need of a second hand to actuate a second plunger of another syringe. Accordingly, manual actuation of the plunger 180, in combination with the locking element 162 and the biased accumulator 114, cooperate to agitate the liquid embolic composition within the syringe device 110, requiring the use of only one hand.

The liquid embolic composition is transferred from the second syringe 116 to the catheter 118 for injection into a vascular site. During transfer to the catheter 118, the valve 120 is in position G, illustrated in FIG. 2d. The port 188a is sealed off, preventing the liquid embolic composition from entering the first syringe 112. As the plunger 180 is selectively advanced towards the distal end 170 in the direction of arrow 199 (i.e., an empty position), the pressure applied to the plunger 180 provides a force which pushes the predetermined volume of liquid embolic composition out of the second syringe 116 and into the catheter 118. Due to the positioning of the valve 120, the liquid embolic composition travels from the second syringe 116, through the port 188c, the bore 190a, the port 188b, the collar 189, and into the catheter 118 for patient delivery.

In one embodiment, the second syringe 116 may include a feature, such as an adjustable detent, or an escapement, configured to limit the travel of the stroke of the plunger 180 within the barrel 168 to allow a selectable or pre-selected fraction of the capacity of the second syringe 116 to be delivered to the catheter 118 for patient delivery. For example, if the second syringe 116 has a capacity of around three cubic centimeters, the adjustable detent may allow a one cubic centimeter bolus of the liquid embolic composition to be administered three successive times before the second syringe 116 will need to aspirate another load of the liquid embolic composition.

Figure 3:
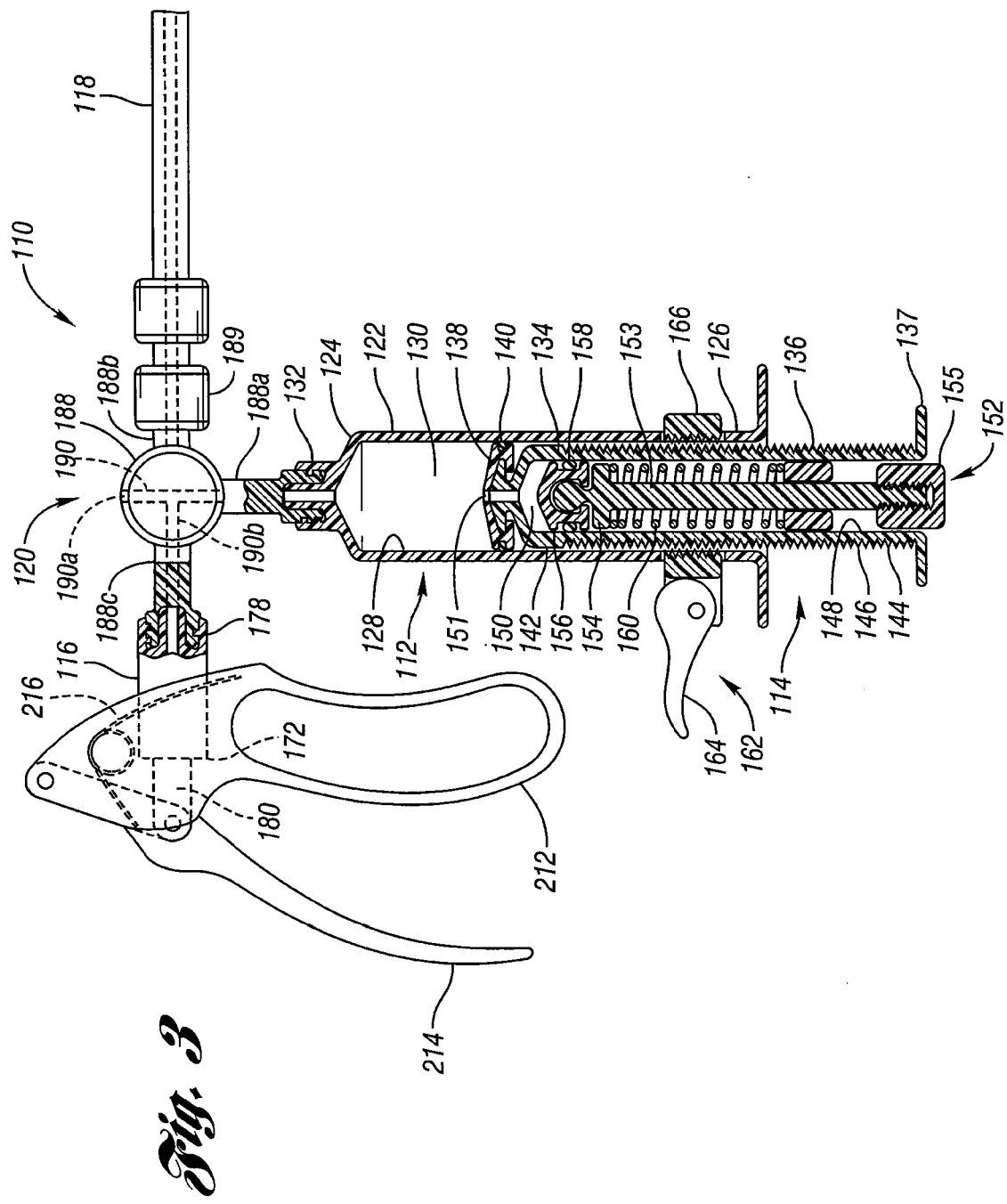
FIG. 3 is a cross-sectional side view of a syringe device in accordance with yet another embodiment of the present invention.

As illustrated in FIG. 3, a handle 212 and a lever 214 are coupled to the second syringe 116 of FIGS. 2a-d. Coupled at the proximal end 172, the handle 212 and the lever 214 cooperate with a spring 216 to assist the operator in applying an actuating force to the plunger 180 to overcome the pressure of the spring-biased piston 156 of the accumulator 114 during agitation. The handle 212 and the lever 214 may also be coupled to the proximal end 42 of the second syringe 14 of FIGS. 1a-d to assist the operator in applying an actuating force to the plunger 50 to overcome the pressure of the spring-biased piston 70 of the accumulator 16 during agitation. In use, the fingers of the operator's hand are positioned through the opening in the handle 212 and the front side of the operator's palm is positioned about the lever 214. The operator squeezes the lever 214 toward the handle 212 to actuate the plunger towards the distal end of the syringe barrel during agitation of the liquid embolic composition.

While the present invention has been described in terms of preferred embodiments, it will be understood, of course, that the invention is not limited thereto since modifications may be made to those skilled in the art, particularly in light of the foregoing teachings.

The invention claimed is:

1. A syringe device for agitating and delivering a liquid medication to a patient comprising:
an injecting member;
a first syringe configured to provide the liquid medication;
a second syringe in selective fluid communication with the injecting member and the first syringe, the second syringe being configured to receive the liquid medication from the first syringe and move the liquid medication to the injecting member for patient delivery, the second syringe also being coupled to the first syringe by a valve, the valve being selectively adjustable between a first position in which the first syringe is in fluid communication with the second syringe and a second position in which the first syringe is not in fluid communication with the second syringe; and
an accumulator in selective fluid communication with the second syringe, the accumulator being biased to an empty position to move the liquid medication to the second syringe by a biasing member, wherein the biasing member is one of a spring, foam, gas, balloon, elastomer, electromagnetic field, and gravity, wherein the biased accumulator cooperates with the second syringe to agitate the liquid medication between the second syringe and the accumulator prior to patient delivery.

2. The device of claim 1, further comprising a first valve coupling the first syringe to the second syringe and a second valve coupling the accumulator to the second syringe proximal the first valve, the first valve being selectively adjustable between a first position in which the first and second syringes are in fluid communication with each other and a second position in which the first and second syringes are not in fluid communication with each other, the second valve being selectively adjustable between a first position in which the accumulator and the second syringe are in fluid communication with each other and the second valve is not in fluid communication with the first valve, a second position in which the accumulator and the second syringe are in fluid communication with each other and the second valve is in fluid communication with the first valve, and a third position in which the accumulator and the second syringe are not in fluid communication with each other and the second valve is in fluid communication with the first valve, wherein the second syringe is in fluid communication with the injecting member when the first valve is in the second position and when the second valve is in the third position.

3. The device of claim 2, wherein the first syringe includes a first barrel having a distal end, an opposing proximal end, and a first tubular tip projecting from the distal end configured to facilitate connection with the first valve, the proximal end being configured to receive a first piston longitudinally slidable within the first barrel,
wherein the second syringe includes a second barrel having a distal end, an opposing proximal end, and a second tubular tip projecting from the distal end configured to facilitate connection with the second valve, the proximal end being configured to receive a second piston longitudinally slidable within the second barrel,
wherein the accumulator includes a third barrel having a distal end, an opposing proximal end, a third tubular tip projecting from the distal end configured to facilitate connection with the second valve, and a third piston longitudinally slidable within the third barrel, the third piston being biased towards the distal end of the third barrel consistent with the empty position.

4. The device of claim 3, wherein manipulation of the second piston towards the distal end of the second barrel withdraws the liquid medication from the first syringe and into the second syringe when the first valve is in the first position and when the second valve is in one of the second position and the third position.

5. The device of claim 3, wherein manipulation of the second piston towards the distal end of the second barrel cooperates with the biased third piston of the accumulator to agitate the liquid medication back and forth between the second syringe and the accumulator when the second valve is in the first position.

6. The device of claim 3, wherein manipulation of the second piston towards the distal end of the second barrel forces the liquid medication from the second syringe to the injecting member for patient delivery when the first valve is in the second position and when the second valve is in the third position.

7. The device of claim 1, wherein first syringe includes a first barrel and a first plunger longitudinally slidable within the first barrel, wherein the second syringe includes a second barrel and a second plunger longitudinally slidable within the second barrel, wherein the accumulator includes a third barrel and a third plunger longitudinally slidable within the third barrel.

8. The device of claim 7, further comprising a handle coupled to the second syringe, the handle being configured to assist an operator to manipulate the second plunger.

9. The device of claim 7, wherein the accumulator is disposed within the first syringe, wherein the first plunger of the first syringe forms the third barrel of the accumulator such that the accumulator is longitudinally slidable within the first syringe.

10. The device of claim 9, further comprising a locking element configured to prevent the accumulator from longitudinally sliding within the first syringe when in a locked position.

11. The device of claim 10, wherein the third barrel of the accumulator includes a threaded outer wall, wherein the locking element includes a threaded member coupled with a cam lever, wherein the threaded member is configured to intersect a portion of the first barrel of the first syringe, wherein the cam lever is configured to selectively engage the threaded member against the threaded outer wall to lock the accumulator in place within the first syringe defining the locked position.

12. The device of claim 10, wherein the valve is selectively adjustable between a first position in which the first syringe and the accumulator are in fluid communication with the second syringe and in which the first syringe, the accumulator, and the second syringe are not in fluid communication with the injecting member, and a second position in which the first syringe and the accumulator are not in fluid communication with the second syringe or the injecting member and in which the second syringe is in fluid communication with the injecting member.

13. The device of claim 12, wherein the first barrel includes a distal end, an opposing proximal end, and a first tubular tip projecting from the distal end configured to facilitate connection with the valve, the proximal end being configured to receive the first plunger, wherein the second barrel includes a distal end, an opposing proximal end, and a second tubular tip projecting from the distal end configured to facilitate connection with the valve, the proximal end being configured to receive the second plunger, wherein the third barrel includes a distal end, an opposing proximal end, and a channel formed through the distal end providing a fluid communication between the first syringe and the accumulator, the proximal end being configured to receive the third plunger, the third plunger being biased towards the distal end of the third barrel consistent with the empty position.

14. The device of claim 13, wherein manipulation of the second plunger towards the proximal end of the second barrel withdraws the liquid medication from the first syringe and into the second syringe when the valve is in the first position and when the locking element is in an unlocked position.

15. The device of claim 13, wherein manipulation of the second plunger towards the distal end of the second barrel forces the liquid medication from the second syringe to the injecting member for patient delivery when the valve is in the second position.

16. The device of claim 13, wherein manipulation of the second plunger towards the distal end of the second barrel cooperates with the biased third plunger and the locking element to agitate the liquid medication back and forth between the second syringe and the accumulator when the valve is in the first position and when the locking element is in the locked position.

17. A syringe device for agitating and delivering a liquid medication to a patient comprising:
   an injecting member;
   a first syringe configured to provide the liquid medication, the first syringe having a first barrel including a first plunger longitudinally slidable within the first barrel;
   a second syringe configured to fluidly communicate with the injecting member and the first syringe, the second syringe being configured to receive the liquid medication from the first syringe and move the liquid medication to the injecting member for patient delivery, the second syringe having a second barrel including a second plunger longitudinally slidable within the second barrel;
   an accumulator configured to fluidly communicate with the second syringe, the accumulator including a third barrel having a third plunger longitudinally slidable within the third barrel, the third plunger being biased to an empty position to move the liquid medication to the second syringe, wherein the first plunger of the first syringe forms the third barrel of the accumulator such that the accumulator is longitudinally slidable within the first syringe;
   a locking element configured to prevent the accumulator from longitudinally sliding within the first syringe when in a locked position; and
   a valve coupling the first syringe to the second syringe, the valve being selectively adjustable between a first position in which the first syringe and the accumulator are in fluid communication with the second syringe and in which the first syringe, the accumulator, and the second syringe are not in fluid communication with the injecting member, and a second position in which the first syringe and the accumulator are not in fluid communication with the second syringe or the injecting member and in which the second syringe is in fluid communication with the injecting member.

18. A method of agitating and delivering a liquid medication to a patient comprising the steps of:
   providing a syringe device including:
      an injecting member;
      a first syringe configured to provide the liquid medication;
      a second syringe configured to receive the liquid medication from the first syringe and move the liquid medication to the injecting member for patient delivery, the second syringe also being coupled to the first syringe by a valve, the valve being selectively adjustable between a first position in which the first syringe is in fluid communication with the second syringe and a second position in which the first syringe is not in fluid communication with the second syringe; and
      an accumulator configured to receive a portion of the liquid medication and to agitate the liquid medication back and forth between the accumulator and the second syringe, the accumulator being biased to an empty position to move the liquid medication to the second syringe by a biasing member, wherein the biasing member is one of a spring, foam, gas, balloon, elastomer, electromagnetic field, and gravity;
   transferring the liquid medication from the first syringe to the second syringe;
   shuttling the liquid medication back and forth between the second syringe and the biased accumulator; and
   transferring the liquid medication from the second syringe to the injecting member for patient delivery.

19. The method of claim 18, wherein the accumulator is slidably disposed within the first syringe.

20. The method of claim 18, wherein the syringe device further comprises a locking element configured to prevent the accumulator from longitudinally sliding within the first syringe when in a locked position.

21. A syringe device for agitating and delivering a liquid medication to a patient comprising:
   an injecting member;
   a first syringe configured to provide the liquid medication;
   a second syringe in selective fluid communication with the injecting member and the first syringe, the second syringe being configured to receive the liquid medication from the first syringe and move the liquid medication to the injecting member for patient delivery, the second syringe also being coupled to the first syringe by a valve, the valve being selectively adjustable between a first position in which the first syringe is in fluid communication with the second syringe and a second position in which the first syringe is not in fluid communication with the second syringe, the second syringe having a distal end and being coupled to the valve and the first syringe by a tip projecting from the distal end; and
   an accumulator in selective fluid communication with the second syringe, the accumulator being biased to an empty position to move the liquid medication to the second syringe, wherein the biased accumulator cooperates with the second syringe to agitate the liquid medication between the second syringe and the accumulator prior to patient delivery.

* * * * *